(12) United States Patent
Detry

(10) Patent No.: US 10,085,757 B2
(45) Date of Patent: Oct. 2, 2018

(54) COMPACT DRIVER FOR POWERED SURGICAL TOOL

(71) Applicant: Zimmer Surgical SA, Geneva (CH)

(72) Inventor: Marc Detry, Ayze (FR)

(73) Assignee: Zimmer Surgical SA (CH)

(*) Notice: Subject to any disclaimer, the term of this patent is extended or adjusted under 35 U.S.C. 154(b) by 665 days.

(21) Appl. No.: 13/966,646

(22) Filed: Aug. 14, 2013

(65) Prior Publication Data

US 2013/0325013 A1    Dec. 5, 2013

Related U.S. Application Data

(63) Continuation of application No. PCT/EP2012/052434, filed on Feb. 13, 2012.

(30) Foreign Application Priority Data

Feb. 15, 2011  (EP) .................................. 11154452
Apr. 19, 2011  (EP) .................................. 11163072

(51) Int. Cl.
    *A61B 17/16*    (2006.01)
(52) U.S. Cl.
    CPC ...... *A61B 17/1628* (2013.01); *A61B 17/1624* (2013.01); *Y10T 29/49117* (2015.01); *Y10T 74/2186* (2015.01)
(58) Field of Classification Search
    CPC .......... B25F 5/02; H02K 1/2786; B25B 45/00
    USPC ....................................................... 173/217
    See application file for complete search history.

(56) References Cited

U.S. PATENT DOCUMENTS

| 3,622,822 A | * | 11/1971 | Lofstrand | ................ H02K 5/08 |
| | | | | 310/43 |
| 3,734,207 A | | 5/1973 | Fishbein | |
| 4,209,721 A | * | 6/1980 | Feldle | ..................... F16C 19/08 |
| | | | | 310/67 R |

(Continued)

FOREIGN PATENT DOCUMENTS

| DE | 20 2007 004 491 U1 | 8/2007 |
| WO | 9805261 A2 | 2/1998 |

(Continued)

OTHER PUBLICATIONS

"European Application Serial No. 11163072.9, Extended European Search Report dated Sep. 19, 2011", 6 pgs.

(Continued)

*Primary Examiner* — David Bates
(74) *Attorney, Agent, or Firm* — Schwegman Lundberg & Woessner, P.A.

(57) ABSTRACT

A motor and gearbox assembly, including a motor, a support fixedly attached to the motor for supporting the motor, a gearbox coupled to the motor, and a casing at least partly enclosing the gearbox. The support includes a cylindrical front end coaxially aligned with the motor's rotation axis and having attachment means formed thereon. The casing includes a cylindrical back end having attachment means formed thereon for attachment with the attachment means of the support. The attachments means of the support and the attachment means of the casing are circular and coaxially aligned with the motor's rotation axis. A driver for a powered surgical tool having such a motor and gearbox assembly is also disclosed.

14 Claims, 2 Drawing Sheets

(56) References Cited

U.S. PATENT DOCUMENTS

| | | | |
|---|---|---|---|
| 5,207,697 A | 5/1993 | Carusillo et al. | |
| 5,712,518 A | 1/1998 | Heckele et al. | |
| 5,747,953 A * | 5/1998 | Philipp | A61B 17/1626 318/114 |
| 5,975,218 A * | 11/1999 | Liau | B25F 3/00 173/216 |
| 5,993,454 A * | 11/1999 | Longo | A61B 17/1624 606/80 |
| 6,553,642 B2 * | 4/2003 | Driessen | B25F 3/00 173/217 |
| 6,716,215 B1 * | 4/2004 | David | A61B 17/1622 433/116 |
| 6,958,071 B2 * | 10/2005 | Carusillo | A61B 17/32002 606/170 |
| 8,074,735 B2 * | 12/2011 | Aeberhard | B25B 21/00 173/104 |
| 8,695,725 B2 * | 4/2014 | Lau | B25F 3/00 173/170 |
| 8,696,511 B2 * | 4/2014 | Steele | A61B 17/7082 475/14 |
| 8,894,654 B2 * | 11/2014 | Anderson | A61B 17/1626 173/176 |
| 9,800,116 B2 * | 10/2017 | Iwai | H02K 9/06 |
| 2001/0043806 A1 * | 11/2001 | Gorti | H02K 3/47 388/800 |
| 2002/0050368 A1 * | 5/2002 | Driessen | B25F 3/00 173/217 |
| 2003/0066667 A1 * | 4/2003 | Zhang | B25F 3/00 173/217 |
| 2003/0222516 A1 * | 12/2003 | Cleanthous | H02K 3/47 310/50 |
| 2004/0191010 A1 * | 9/2004 | Mazaki | B23B 51/02 408/1 R |
| 2008/0077149 A1 * | 3/2008 | Hoegerle | A61B 17/1613 606/80 |
| 2009/0096401 A1 * | 4/2009 | Watabe | B25F 5/00 318/446 |
| 2009/0126964 A1 * | 5/2009 | Schroeder | B25F 5/02 173/217 |
| 2009/0133894 A1 * | 5/2009 | Mizuhara | B25B 21/02 173/217 |
| 2010/0090554 A1 * | 4/2010 | Yano | H02K 21/222 310/156.01 |
| 2010/0105287 A1 * | 4/2010 | Nordstrom | B24B 23/00 451/1 |
| 2010/0253162 A1 * | 10/2010 | Sakamaki | B25D 16/00 310/50 |
| 2013/0207491 A1 * | 8/2013 | Hatfield | H02K 11/33 310/50 |
| 2013/0284479 A1 * | 10/2013 | Chen | B25F 5/02 173/217 |
| 2013/0287509 A1 * | 10/2013 | Guerin | B23Q 5/225 408/57 |
| 2014/0361645 A1 * | 12/2014 | Beyerl | H02K 7/145 310/50 |

FOREIGN PATENT DOCUMENTS

| | | |
|---|---|---|
| WO | WO-2007002230 A1 | 1/2007 |
| WO | 2010028001 A2 | 3/2010 |

OTHER PUBLICATIONS

"European Application Serial No. 11163072.9, Noting of loss of rights mailed Apr. 4, 2013", 2 pgs.

"European Application Serial No. 12703138.3, Communication Pursuant to Article 94(3) EPC dated Jun. 2, 2016", 3 pgs.

"European Application Serial No. 12703138.3, Response filed Dec. 20, 2014 to Communication Pursuant to Rules 161(1) and 162 EPC dated Oct. 2, 2013", 13 pgs.

"International Application Serial No. PCT/EP2012/052434, International Preliminary Report on Patentability dated May 27, 2013", 13 pgs.

"International Application Serial No. PCT/EP2012/052434, International Search Report dated Jul. 13, 2012", 6 pgs.

"International Application Serial No. PCT/EP2012/052434, Written Opinion dated Jul. 13, 2012", 8 pgs.

"European Application Serial No. 12703138.3, Response filed Oct. 12, 2016 to Communication Pursuant to Article 94(3) EPC dated Jun. 2, 2016", 13 pgs.

* cited by examiner

COMPACT DRIVER FOR POWERED SURGICAL TOOL

CROSS-REFERENCE TO RELATED APPLICATIONS

This application is a continuation of PCT/EP2012/052434, filed on Feb. 13, 2012, which claims priority to EP 11154452.4, filed on Feb. 15, 2011 and EP 11163072.9 filed on Apr. 19, 2011, the entire disclosures of which are incorporated herein by reference.

TECHNICAL FIELD

The present disclosure relates to a powered surgical tool. The present disclosure relates in particular to a driver for surgical tools enclosing a compact gearbox and motor assembly.

BACKGROUND

Powered surgical tools, for example powered surgical saws and/or drills are powered tools that surgeons employ for performing certain surgical procedures that include cutting and/or drilling bones and/or other tissues. A powered surgical tool typically comprises a handpiece, or driver, in which is housed a motor, for example an electrically or pneumatically driven motor. The motor is attached, for example through a drive shaft, to a head of the driver, which is adapted to removably receive a surgical tool, for example a saw blade or a drill bit. Depending on the configuration of the driver and/or the nature of the attached tool, the actuation of the motor causes an oscillating or rotating movement of the head and thus of the tool.

Powered surgical tools are able to cut or drill through both hard and soft tissue much faster and with greater accuracy than manually operated tools. Powered surgical tools are furthermore able to perform specific cuts that manually operated tools are unable to perform. Also, the physical effort a surgeon has to employ to operate a powered surgical tool is much less than that used when cutting or drilling tissue, including bones, with a manual tool.

However, in order to provide enough power and/or torque to the tool for performing specific operations, the motor, in particular the electrical motor, is often dimensioned large relative to the tool, which in turn makes the driver housing the motor relatively bulky and thus sometimes inappropriate or at least inconvenient for delicate operations.

U.S. Pat. No. 5,993,454 for example describes a drill attachment for a surgical drill, which comprises a gear assembly for transferring the rotational power developed by the drill's shaft to a chuck mounted to the front of the drill attachment. From the figures, it seems that the drill attachment is coupled to the drill through a bayonet mechanism. The surgical drill illustrated in this document is however rather bulky. The drill comprises a motor and a gear train, but there is no indicating on how these elements are assembled and/or attached inside the surgical drill.

U.S. Pat. No. 5,207,697 describes a pistol-shaped surgical handpiece, in which a motor and a gear box, or reducer unit, are both inserted in a same cylindrical support shell. After its insertion into the shell, the motor is axially pressed between an intermediate baffle located inside the shell and a rear plug closing an extremity of the shell. The motor is thus axially fixed but fits radially loosely within the shell. This construction thus does not allow a precise positioning of the motor inside the handpiece, which is critical in order to achieve precise operations with the tools attached thereto. Furthermore, this attachment of the motor inside the shell requires the use of inrunner motors, which are bulkier than outrunner motor, because the motor is pressed by both extremities which must thus be static elements, i.e. part of an external stator.

German document DE 20 2007 004 491 U1 describes a surgical instrument using an outrunner motor. There is however no indication on how this solution is implemented. In particular, there is no indication on how the out runner motor is attached in the instrument or on how the outrunner is assembled with a gearbox in order to minimize the instrument's dimensions.

SUMMARY

It is thus an object of the present disclosure to provide a compact powered surgical tool, more specifically to provide a compact driver for a powered surgical tool, having smaller dimensions than prior art drivers for similar or better power and/or torque characteristics.

It is another object of the present disclosure to provide a precise and reliable compact powered surgical tool, more specifically to provide a precise and reliable compact driver for a powered surgical tool.

It is a further object of the present disclosure to provide a powered surgical tool, more specifically to provide a driver for a powered surgical tool, having a construction that allows the use of compact elements, such as for example outrunner motors.

This object and other advantages are achieved by a motor and gearbox assembly, a driver for a powered surgical tool, a powered surgical tool, a surgical tool kit and a method for assembling a driver for a powered surgical tool comprising the features of the corresponding independent claims.

These objects are achieved in particular by a motor and gearbox assembly, comprising a motor with a rotation axis, a support for supporting the motor, wherein the motor is fixedly attached to the support and wherein the support comprises a cylindrical front end coaxially aligned with the motor's rotation axis and having attachment means formed thereon, a gearbox coupled to the motor and a casing at least partly enclosing the gearbox and comprising a cylindrical back end with attachment means formed thereon for attachment with the attachment means of the support, wherein the attachment means of the support and the attachment means of the casing are circular and coaxially aligned with the motor's rotation axis.

These objects are also achieved by a driver for a powered surgical tool, comprising such a motor and gearbox assembly comprising a cylindrical front end with attachment means formed thereon, positioned around the rotation axis of the motor and gearbox assembly, a tool chuck for receiving a surgical tool, coupled to the gearbox and comprising a cylindrical back end with attachment means formed thereon for attachment with the attachment means of the motor and gearbox assembly, and a cover at least partly enclosing the tool chuck and/or the motor and gearbox assembly, wherein the attachment means of the motor and gearbox assembly and the attachment means of the tool chuck are circular and coaxially aligned with the rotation axis of the motor and gearbox assembly. These attachment means for example comprise a threaded front end of the casing and a threaded back end of the tool chuck.

These objects are also achieved in particular by a surgical tool kit, comprising such a driver and a plurality of surgical tools for use with the driver.

These objects are also achieved in particular by a method for assembling such a driver comprising the steps of attaching the motor to the support, inserting the gearbox inside the casing, coupling the gearbox to the motor by attaching the front end of the support to the back end of the casing and coupling the gearbox to the tool chuck by attaching the front end of the casing to the back end of the tool chuck. The step of coupling the gearbox to the motor for example comprises rotating the casing relative to the support for screwing the front end of the support onto the back end of the casing. Similarly, the step of coupling the gearbox to the tool chuck comprises rotating the casing relative to the tool chuck for screwing the front end of the casing onto the back end of the tool chuck.

Accordingly, the motor and the gearbox being coupled to each other by circular attachment means formed on the periphery of their cylindrical casing or support, these attachment means being for example a threaded front end of the support and a threaded back end of the casing, the radial dimension of the assembly is kept to a minimum, thereby allowing minimizing the overall dimensions of the driver. In other embodiments, the attachment means comprises ridges and/or ribs formed on the periphery of front end of the support and ribs and/or ridges formed on the periphery of the back end of the casing.

In embodiments, the motor of the motor and gearbox assembly is an outrunner motor, thus allowing the use of a particularly compact motor.

The support for the motor for example comprises fastening means for attaching a static front end of the motor to it, thereby minimizing the space required for fastening the motor to the support. The fastening means for example comprise screws and the static front end of the motor is screwed onto the support.

In embodiments of the driver, the cover comprises alignment and/or antirotation means for positioning and attaching the motor and gearbox assembly and the tool chuck relative to the cover when the motor and gearbox assembly is coupled to the tool chuck. The alignment means for example comprises a shoulder formed inside the cover, which is firmly pinched between the motor and gearbox assembly on one side and the tool chuck on the other side when the motor and gearbox assembly is coupled to the tool chuck. This allows attaching the motor and gearbox assembly and the tool chuck inside the driver in an easy manner requiring little space. The alignment and/or antirotation means for example further comprises pins that extend in corresponding bores of the tool chuck when the motor and gearbox assembly is coupled to the tool chuck in order to avoid unwanted rotation of the assembly while the tool is in use.

In embodiments, the powered surgical tool is a drill bit and the drive shaft or axis of the motor (2) is cannulated for allowing the insertion of a drill bit, thereby allowing the use for example of K-wires for drilling long and very thin holes. The motor is for example an outrunner motor.

In embodiments, the powered surgical tool is a saw blade.

Any combination of the above embodiments and variants is possible within the frame of the invention.

BRIEF DESCRIPTION OF THE DRAWINGS

The above and further advantages of the disclosed solution will be better understood by reference to the following description illustrated by the figures, where.

DETAILED DESCRIPTION

Figure 1:
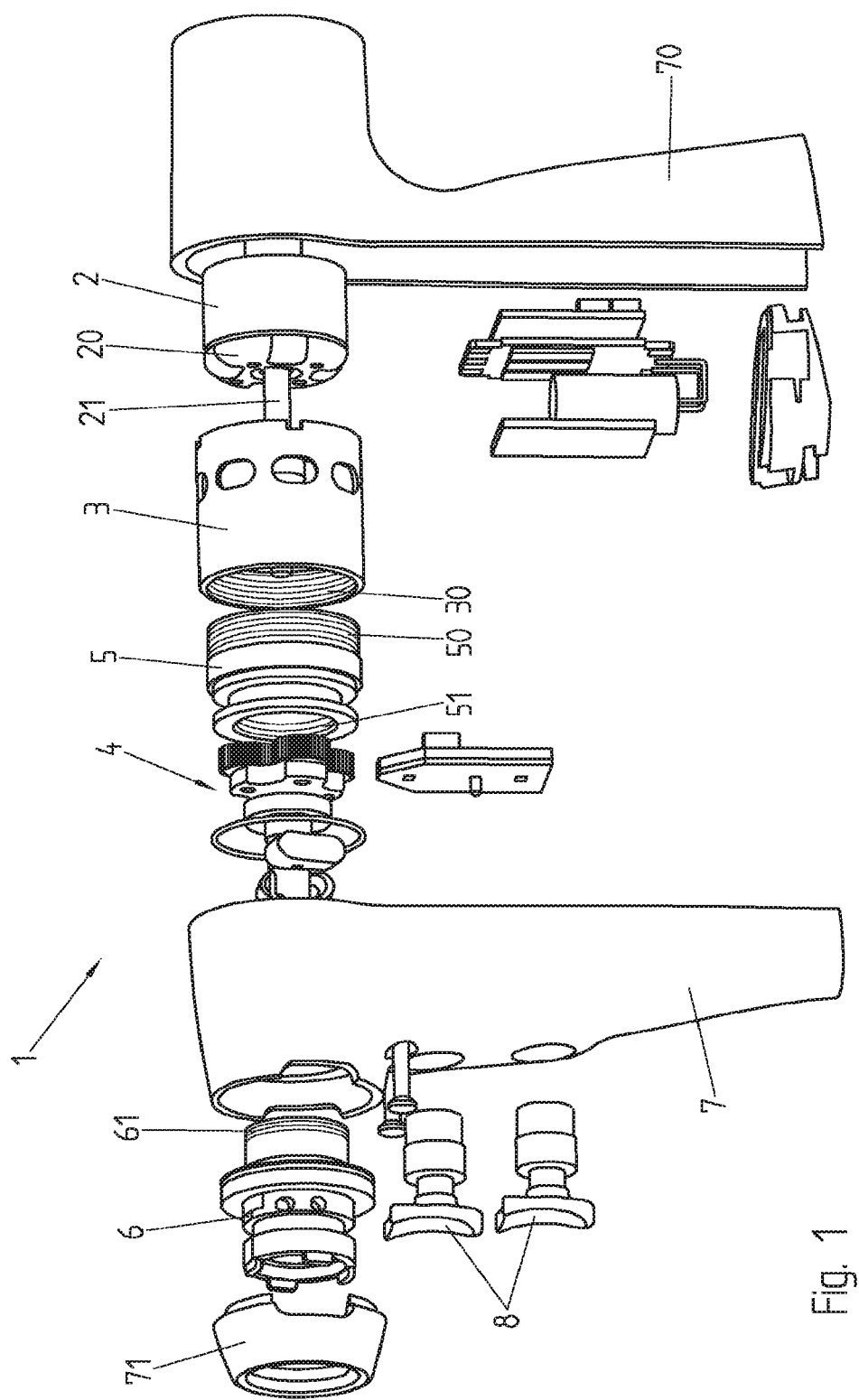
FIG. 1 is an exploded view of an illustrative but not limiting example of a driver according to an exemplary embodiment.
Figure 2:
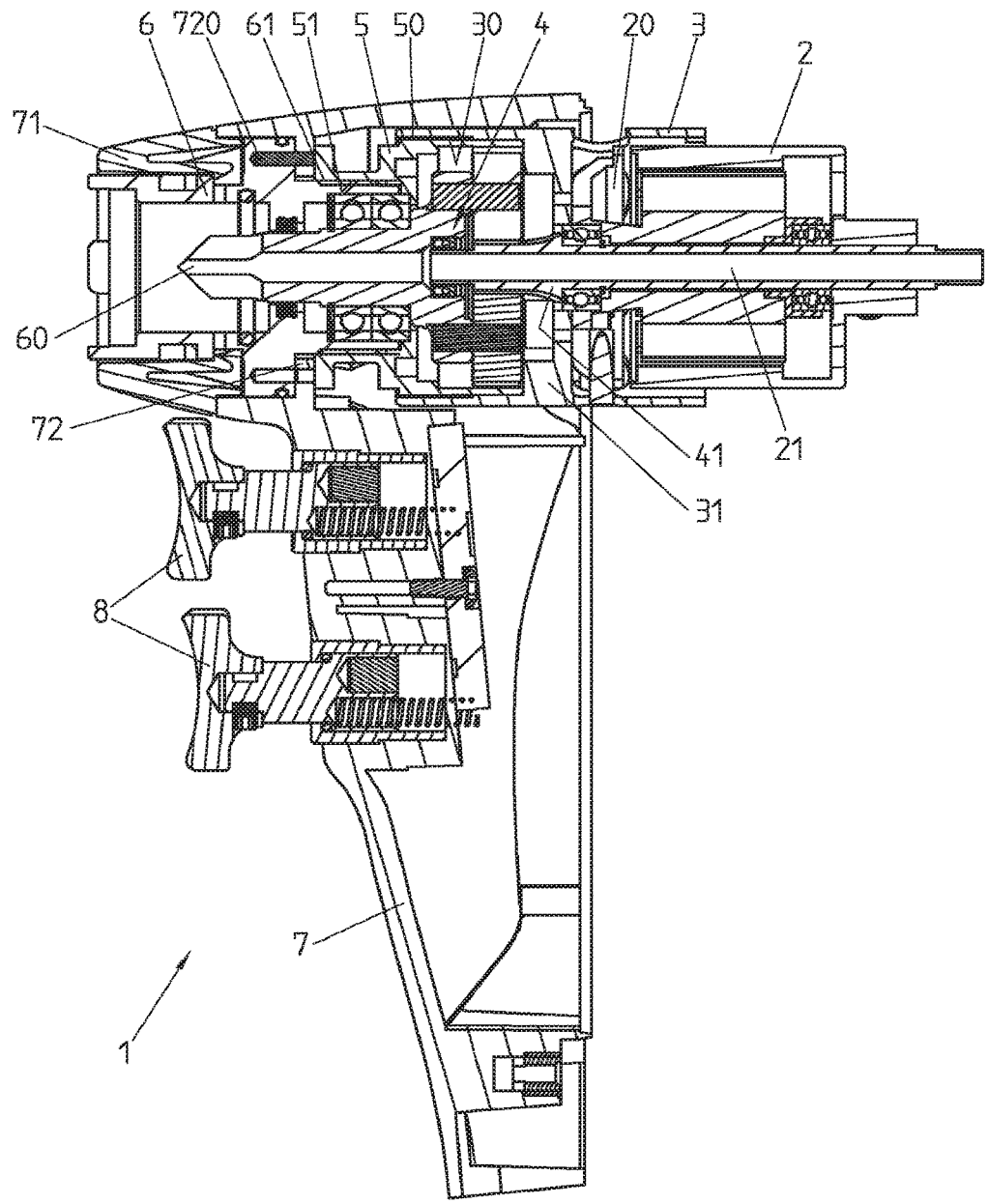
FIG. 2 is a cut view of the partly assembled driver of FIG. 1.

With reference to the figures illustrating an exemplary embodiment, the driver 1 comprises a motor 2, for example an electrically powered motor. In an embodiment, the motor 2 is a brushless outrunner motor. Outrunner motors, also known as external-rotor motors, are electrical motors wherein the stator forms the center, or core, of the motor, while an overhanging rotor surrounds the core. The stator for example comprises coils while the rotor comprises permanent magnets. Outrunner motors with given power output characteristics can have smaller dimensions than inrunner motors with similar characteristics. Using an outrunner motor thereby allows the construction of a more compact driver for given power characteristics.

The motor 2 is coupled to a tool chuck 6 through a gearbox 4, for example a planetary gearbox. The tool chuck 6 is configured to receive a surgical tool, which is not represented in the figures.

In the illustrated example, the tool chuck 6 is configured for receiving a drill bit and transmitting the motor's and gearbox's rotational movement to the drill bit. In other embodiments, the tool chuck is configured for receiving a saw blade and transforms the rotational movement of the motor and gearbox into a laterally oscillating movement that allows the cutting action of the blade.

The motor 2 is attached to a support 3 that comprises a cylindrical threaded front end 30 coaxially aligned with the motor's axis when the motor 2 is attached to the support 3. The support 3 is located around and/or in front of the output side, or front end 20, of the motor 2. In the illustrated embodiment, the support 3 is an essentially cylindrical element defining a cylindrical passageway therein, with fastening means for fixedly attaching the motor 2 inside the passageway. The support 3 is made for example of metal, metal alloy or any ridged material, sufficiently resistant mechanically for supporting the motor 2.

According to the illustrated exemplary embodiment, the motor 2 is an outrunner motor with a static front end 20. The static front end 20 is for example integral with the motor's stator. The outrunner motor 2 is at least partly inserted in the passageway of the support 3 and fixedly attached, for example screwed, with its front end 20 to the support 3. The motor 2 is for example fixedly attached to a shoulder 31 inside the passageway of the support 3. The fastening means for fixedly attaching the motor 2 to the support 3 are for example screws that extend through bores in the shoulder 31 and into correspondingly threaded holes in the front end 20 of the motor 2. The motor 2 is thus for example attached with its static front end 20 to the shoulder 31 by means of multiple screws arranged around the rotation axis 21 of the motor 2.

The shoulder 31 for example comprises alignment means for correctly aligning axially and/or radially the motor 2 relative to the support 3 when the motor 2 is attached to the support 3. In variant embodiments, alignment means can for example comprise a precise position of the screws for attaching the motor 2, and/or a tight fit between at least part of the motor 2 and the passageway inside the support 3, etc. A combination of these alignment means is also possible. In an embodiment, the rotation axis 21 of the motor 2 extends beyond the shoulder 31, towards the threaded front end 30 of the support 3.

Attaching the motor 2 with its front end 20, i.e. closer to the gearbox 4, helps reducing alignment errors, play, vibrations and other disturbances on the output side of the motor 2, thereby providing for a more precise and smoother functioning of the driver 1 and thus of the powered surgical tool.

The power to size ratio of outrunner motors is particularly advantageous for their use in a compact device, for example in a compact motor and gearbox assembly as discussed in the present disclosure. However, a drawback of outrunner motors is that their rotor forms most of their external surface, thereby limiting the number of attachment possibilities to a support. Their front end is often their only static part accessible from the outside. Fastening, or attaching, the front end 20 of the motor 2 to the support 3, apart from resulting in a compact construction, is thus particularly well suited to the use of outrunner motors. In embodiments, the support 3 extends over the motor 2 when the motor 2 is fastened to the support 3, thereby providing mechanical protection to the rotor rotating inside the support 3 when the motor 2 is in use.

The gearbox 4 is for example a planetary gearbox whose central gear, or sun gear 41, is driven by, for example integral with, the axis 21 of the motor 2 while the planet gear carrier is coupled to, for example integral with, a coupling element 60 of the tool chuck 6 configured to drive an attached tool. In this configuration, the gearbox 4 is configured to reduce the rotation speed of the tool chuck compared to that of the motor 2, thereby increasing the available torque. The reduction ratio is for example one to six or one to seven. Other values are however possible depending on the motor's characteristics and/or on the desired characteristics of the surgical tool. According to other embodiments, the gearbox is configured for increasing the rotation speed of the tool chuck compared to that of the motor, for example in that the axis of the motor drives the planet gear carrier of the gearbox while the sun gear is coupled to and drives the coupling element.

The gearbox 4 is at least partly contained in and aligned relative to a casing 5 that comprises a cylindrical threaded back end 50 coaxially aligned with the rotation axis of the sun gear 41 and located around the input side, or back side, of the gearbox 4. In the illustrated embodiment, the casing 5 is an essentially cylindrical element defining a cylindrical passageway therein. The gearbox 4 is for example held inside the casing 5 through a ball bearing supporting the axis of the planet gear carrier in a determined position. Any other suitable type of holding means may however be used within the frame of the invention in order to hold the elements of the gearbox within the casing. A gear ring is formed on at least part of the inner surface of the casing 5 and meshed with the planet gears, thus acting as a fixed annulus of the planetary gearbox 4. In variant embodiments, for example, the annulus of the planetary gearbox is a gear ring whose external dimensions are chose for a tight fit inside the casing.

The casing 5 is made for example of metal, metal alloy or any rigid material, sufficiently resistant mechanically for supporting the gearbox 4. In an embodiment, the material of the casing 5 is the same as the material of the support 3.

In an embodiment, the gearbox 4 is coupled to the motor 2 in that the threaded front end 30 of support 3 is screwed onto the threaded back end 50 of casing 5 by rotating support 3 relative to casing 5. Attachment means other than threads are however possible. In variant embodiments, the casing of the gearbox is for example clipped onto the support of the motor, in that for example one or more protruding ribs around the periphery of the casing and/or of the support is inserted into one or more corresponding ridges on the periphery of the support and/or of the casing respectively. The use of circular attachment means coaxial with the motor's rotation axis, such as threads and/or ribs and ridges that are directly formed on the periphery of the corresponding ends of the casing and of the support, allows minimizing the overall radial dimension of the motor and gearbox assembly because the attachment means do not protrude radially from the support 3 and/or the casing 5. It also facilitates the assembly of the motor 2 to the gearbox 4.

According to some embodiments, the casing 5 is attached to the tool chuck 6 using similar attachment means than those described above and used for attaching the casing 5 to the support 3.

In an embodiment, the front end 51 of the casing 5 is thus cylindrical and threaded on its internal side, while the back end 61 of the tool chuck 6 is also cylindrical but threaded on its external side. The casing 5 is then attached to the tool chuck 6 by screwing them onto each other by rotating the casing 5 relative to the tool chuck 6. In a variant embodiment, the front end 51 of the casing 5 is threaded on its external side, while the back end 61 of the tool chuck 6 is threaded on its internal side. Other circular attachment means directly formed on the periphery of the casing 5 and of the tool chuck 6, such as for example ridges and ribs, are however possible in other embodiments.

According to the illustrated exemplary embodiment, the casing 5 and the tool chuck 6 are attached to each other inside a chassis and/or a cover 7 of the driver 1, which forms at least part of the external skin of the driver 1, and each of the casing 5 and the tool chuck 6 holds onto an opposite side of a shoulder 72 formed inside for example the cover 7. When attaching the casing 5 and the tool chuck 6 to each other, the tool chuck 6 is thus for example inserted into the corresponding part of the cover 7 through the front end of the driver 1, while the casing 6 is inserted from the back end, thereby each approaching the shoulder 72 from another side. The casing 5 is screwed or otherwise attached to the tool chuck 6, until the shoulder 72 is for example tightly held between corresponding shoulders of these two elements, thereby attaching the tool chuck 6 and casing 5 assembly to the cover 7.

According to some embodiments, the shoulder 72 further comprises alignment and/or antirotation means for correctly aligning the tool chuck 6 and casing 5 assembly inside the driver 1 and/or for avoiding an undesired rotation of the assembly inside the cover 7 once the driver is assembled and for example in use. These means comprise for example pins 720 extending from at least one of its sides, for example on the side of the tool chuck 6, into corresponding bores of the respective element, for example of the tool chuck 6. Accordingly, when assembling the illustrated exemplary driver 1, the tool chuck 6 is advantageously inserted first inside the cover 7 and correctly placed against the shoulder 72 with the pins 720 inserted in the corresponding bores. The casing 5 is then inserted in the cover 7 from the other side and screwed with its front end 51 onto the back end 61 of the tool chuck 6 until the shoulder 72 is tightly gripped. In variant embodiments, the motor 2 may already be assembled with the gearbox 4 before the gearbox 4 is coupled to the tool chuck 6 by attaching the casing 5 to the tool chuck 6.

For aesthetic and/or hygienic reasons, the front end of the tool chuck 6 is then at least partly covered by a nose cap 71 that attaches, for example clips, onto the corresponding end of the cover 7. The cover 7, the nose cap 71 and the back cover 70 closing the housing of the driver 1 are for example made of molded synthetic material, for example plastic or other material adapted to medical applications.

Accordingly, in the assembled driver 1, the tool chuck 6, the gearbox 4 and the motor 2 are aligned along the direction of the motor's rotation axis in the housing formed by the cover 7, the back cover 70 and the nose cap 71. The gearbox 4 is coupled to the motor 2 in that the support 3 holding the motor 2 is screwed or clipped onto the casing 5 supporting the gearbox 4, for example by a thread and nut connection formed directly on the periphery of the corresponding ends of support 3 and casing 5, thereby minimizing the radial dimension of the assembly. The gearbox 4 is in turn similarly coupled to the tool chuck 6, the tool chuck 6 and casing 5 assembly furthermore firmly holding onto a part, for example a shoulder 72, of the cover 7. The shoulder 72, or other means for aligning and/or holding the tool chuck 6, gearbox 4 and motor 2 assembly inside the driver 1, can be placed at other locations inside the driver 1. For example it could be pinched by the connection between casing 5 and support 3. An advantage however of placing these positioning and holding means close to the tool chuck 6 is that it is closer to the tool where important forces are exerted, thereby insuring a better stability to the driver 1 and thus to the surgical tool when used.

In order to guarantee tightness of the driver 1 and avoid infiltrations of various fluids inside the cover 7, o-ring joints are located for example around the rotation axes of the coupling element 60 inside the tool chuck 6 and/or around the rotation axis 21 of motor 2, preferably close to the connection to the gearbox 4.

The driver 1 further comprises for example push buttons 8 for actuating and controlling the motor 2 via a controller (not represented on the figures). The driver 1 preferably also comprises an energy source, for example one or more electrical batteries, for powering the motor 2, or a connection to such a power source, for example electrical contacts to one or more external batteries and/or a power cord.

In embodiments, the motor axis, or drive shaft 21 is cannulated in that a longitudinal bore is made on the entire length of the axis. This embodiment is particularly advantageous for use in a driver for a powered surgical drill, since it allows the passage of long drill bits, for example of K-wires, through the bore. Similar bores are also preferably made in the center of the sun gear 41 and of the coupling element 60, which are then aligned with the bore in the motor axis 21 when the driver is assembled. Long drill bits such as for example flexible drill bits or K-wires are for example used during orthopedic operations requiring long and thin holes to be drilled in a bone. In order to achieve high precision drilling, the length of the drill bit protruding out of the tool chuck 6 is adapted at intervals during the drilling operation to the length of the hole. The drill bit is thus pulled little by little out of the tool. The remaining length of the drill bit must thus be stored inside the tool, in the prolongation of the tool chuck. The cannulated coupling element 60, sun gear 41 and motor axis 21 thus from a cylindrical bore in which the unused length of the drill bit, in particular of the K-wire, can be stored during the drilling operation.

The invention claimed is:

1. A motor and gearbox assembly, comprising:
   a motor with a rotation axis, wherein said motor is an outrunner motor;
   a cylindrical support for supporting said motor, said support comprising a cylindrical passageway defined therein and a cylindrical front end coaxially aligned with said rotation axis and having attachment means formed thereon, wherein said motor is positioned at least partly within the cylindrical passageway and is fixedly attached to said support;
   a gearbox coupled to said motor;
   a casing at least partly enclosing said gearbox and comprising a cylindrical back end having attachment means formed thereon for attachment with the attachment means of said support; and
   a rigid cover including a front cover portion engaged with a back cover portion and at least partly enclosing said casing and said support, said front and back cover portions further defining a handle portion extending inferiorly from said casing and said support that is adapted to be grasped by a user;
   wherein said attachment means of said support and said attachment means of said casing are circular and coaxially aligned with said rotation axis.

2. The motor and gearbox assembly according to claim 1, wherein said support is attachable to a static front end of said motor.

3. The motor and gearbox assembly according to claim 2, further comprising one or more screws, wherein said static front end of said motor is screwed onto said support.

4. The motor and gearbox assembly according to claim 1, wherein said attachment means are a threaded front end of said support and a threaded back end of said casing.

5. The motor and gearbox assembly according to claim 1, wherein said attachment means comprises ridges and/or ribs formed on the periphery of said front end of said support and ribs and/or ridges formed on the periphery of said back end of said casing.

6. The motor and gearbox assembly according to claim 1, wherein a drive shaft of said motor is cannulated for allowing the insertion of a drill bit.

7. A driver for a powered surgical tool, comprising:
   a motor and gearbox assembly including:
   a motor with a rotation axis, wherein said motor is an outrunner motor;
   a cylindrical support for supporting said motor, said support comprising a cylindrical passageway defined therein and a cylindrical front end coaxially aligned with said rotation axis and having attachment means formed thereon, wherein said motor is positioned at least partly within the cylindrical passageway and is fixedly attached to said support;
   a gearbox coupled to said motor; and
   a casing at least partly enclosing said gearbox and comprising a cylindrical back end having attachment means formed thereon for attachment with the attachment means of said support and a cylindrical front end with attachment means formed thereon, positioned around the rotation axis of said motor and gearbox assembly;
   wherein said attachment means of said support and said attachment means of said casing are circular and coaxially aligned with said rotation axis;
   a tool chuck for receiving a surgical tool, coupled to said gearbox, comprising a cylindrical back end with attachment means formed thereon for attachment with the attachment means of said motor and gearbox assembly; and
   a rigid cover at least partly enclosing said casing and said support;
   wherein said attachment means of said motor and gearbox assembly and said attachment means of said tool chuck are circular and coaxially aligned with said rotation axis;

wherein said attachment means are a threaded front end of said casing and a threaded back end of said tool chuck; and wherein said cover comprises an alignment structure for positioning and attaching said motor and gearbox assembly and said tool chuck relative to said cover.

8. The driver according to claim 7, wherein said alignment structure comprises a shoulder formed inside said cover that is firmly pinched between said motor and gearbox assembly and said tool chuck.

9. The driver according to claim 8, wherein said shoulder comprises pins that extend in corresponding bores of said tool chuck.

10. A driver for a powered surgical tool, comprising:
a motor and gearbox assembly including:
a motor with a rotation axis;
a support for supporting said motor, wherein said motor is fixedly attached to said support and wherein said support comprises a cylindrical front end coaxially aligned with said rotation axis and having attachment means formed thereon;
a gearbox coupled to said motor; and
a casing at least partly enclosing said gearbox and comprising a cylindrical back end having attachment means formed thereon for attachment with the attachment means of said support and a cylindrical front end with attachment means formed thereon, positioned around the rotation axis of said motor and gearbox assembly;
wherein said attachment means of said support and said attachment means of said casing are circular and coaxially aligned with said rotation axis;
a tool chuck for receiving a surgical tool, coupled to said gearbox, comprising a cylindrical back end with attachment means formed thereon for attachment with the attachment means of said motor and gearbox assembly; and a cover at least partly enclosing said tool chuck and/or said motor and gearbox assembly;

wherein said attachment means of said motor and gearbox assembly and said attachment means of said tool chuck are circular and coaxially aligned with said rotation axis;

wherein said attachment means are a threaded front end of said casing and a threaded back end of said tool chuck; and wherein said cover comprises alignment means for positioning and attaching said motor and gearbox assembly and said tool chuck relative to said cover, said alignment means comprising a shoulder formed inside said cover that is firmly pinched between said motor and gearbox assembly and said tool chuck.

11. The driver according to claim 10, wherein said shoulder comprises pins that extend in corresponding bores of said tool chuck.

12. The motor and gearbox assembly according to claim 1, wherein the attachment means of the support comprises an internally threaded surface and the attachment means of the casing comprises an externally threaded surface, and wherein the internally threaded surface and the externally threaded surface form a threaded connection between the support and the casing.

13. The driver according to claim 7, wherein the attachment means of the support comprises an internally threaded surface and the attachment means of the casing comprises an externally threaded surface, and wherein the internally threaded surface and the externally threaded surface form a threaded connection between the support and the casing.

14. The driver according to claim 7, further comprising one or more actuators extending from the cover and adapted to operate the motor.

* * * * *